(12) United States Patent
Li et al.

(10) Patent No.: US 7,998,499 B2
(45) Date of Patent: Aug. 16, 2011

(54) CALCIUM-CONTAINING BONE IMPLANTS

(75) Inventors: Shu-Tung Li, Oakland, NJ (US); Debbie Yuen, Woodcliff Lake, NJ (US); Hui-chen Chen, Wayne, NJ (US)

(73) Assignee: Collagen Matrix, Inc., Franklin Lakes, NJ (US)

( * ) Notice: Subject to any disclaimer, the term of this patent is extended or adjusted under 35 U.S.C. 154(b) by 799 days.

(21) Appl. No.: 11/923,880

(22) Filed: Oct. 25, 2007

(65) Prior Publication Data

US 2009/0112317 A1  Apr. 30, 2009

(51) Int. Cl.
*A61F 2/00* (2006.01)
(52) U.S. Cl. ..................................................... 424/426
(58) Field of Classification Search .................... 424/426
See application file for complete search history.

(56) References Cited

U.S. PATENT DOCUMENTS

| | | | |
|---|---|---|---|
| 4,774,227 A | 9/1988 | Piez et al. | |
| 4,795,467 A | 1/1989 | Piez et al. | |
| 5,231,169 A | 7/1993 | Constantz et al. | |
| 5,425,770 A | 6/1995 | Piez et al. | |
| 5,455,231 A | 10/1995 | Constantz et al. | |
| 5,573,771 A | 11/1996 | Geistlich et al. | |
| 5,776,193 A | 7/1998 | Kwan et al. | |
| 6,187,047 B1 | 2/2001 | Kwan et al. | |
| 6,300,315 B1 | 10/2001 | Liu | |
| 6,417,166 B2 | 7/2002 | Liu | |
| 6,764,517 B2 | 7/2004 | Yamamoto et al. | |
| 6,846,853 B2 | 1/2005 | Shimp | |
| 6,887,488 B2 * | 5/2005 | Cui et al. | 424/426 |
| 2006/0246150 A1* | 11/2006 | Thorne | 424/603 |

* cited by examiner

*Primary Examiner* — Maryam Monshipouri
(74) *Attorney, Agent, or Firm* — Occhiuti Rohlicek & Tsao LLP

(57) ABSTRACT

This invention relates to a method for preparing a porous bone implant containing a calcium-based mineral. The method includes immersing a porous matrix in an acidic solution containing a calcium-based mineral; removing the matrix from the solution; and exposing the matrix to an alkali to neutralize the acidic solution, thereby causing precipitation of the calcium-based mineral to obtain a porous bone implant containing a calcium-based mineral.

6 Claims, No Drawings

CALCIUM-CONTAINING BONE IMPLANTS

BACKGROUND

It is preferred to include synthetic or natural calcium compounds in bone implants to increase bone conductivity, i.e., growth of bone cells. Examples of such calcium compounds include calcium phosphate, calcium sulphate, deproteinated bone (inorganic bone), calcium composites, and calcium carbonate.

Various methods have been developed for preparing bone implants containing calcium compounds. For example, one can coat a metal matrix with calcium phosphate by plasma spraying treatment, a high-cost process. See, e.g., U.S. Pat. No. 6,846,853. As another example, one can prepare a collagen-based implant impregnated with calcium phosphate as follows: dispersing collagen fiber in a phosphate-containing solution, adding a calcium-containing solution at a pH value of higher than 8 to precipitate calcium phosphate, and freeze-drying the collagen-calcium phosphate mixture to form a sponge-like or membrane-like material. See, e.g., U.S. Pat. Nos. 6,764,517; 6,187,047; 5,455,231; 6,417,166; and 6,300,315. The calcium-impregnated bone implants thus obtained can be too brittle to manipulate.

SUMMARY

In one aspect, the present invention features a method for preparing a porous bone implant containing a calcium-based mineral. The method includes immersing a porous matrix in an acidic solution containing a calcium-based mineral; removing the matrix from the solution; and exposing the matrix to an alkali to neutralize the acidic solution, thereby causing precipitation of the calcium-based mineral to obtain a porous bone implant containing a calcium-based mineral. The porous bone implant thus formed has exactly the same configuration as the porous matrix.

The porous matrix can be made from metal (e.g., titanium or titanium alloy) or polymer (e.g., collagen). The pores in the matrix preferably have diameters of 5 μm to 1,000 μm. The acidic solution used to dissolve the calcium-based mineral, e.g., calcium phosphate or apatite, can be prepared either from an organic acid or from a mineral acid. The alkali used to neutralize the acidic solution can be a solution of ammonia, sodium hydroxide, or potassium hydroxide. It also can be gaseous ammonia or gaseous amine.

In another aspect, the present invention features a porous polymer-based bone implant, which includes a porous polymer-based matrix and a calcium-based mineral. The calcium-based mineral is disposed not only on the surfaces of the matrix but also inside its body. In the bone implant, the amount of the calcium-based mineral per unit area on the surfaces is greater than the amount of the calcium-based mineral per unit area inside the body.

The details of one or more embodiments of the invention are set forth in the description below. Other features, objects, and advantages of the invention will be apparent from the description and from the claims.

DETAILED DESCRIPTION

The method of the present invention takes advantage of the fact that most of the calcium-based minerals are soluble in aqueous acidic solutions (pH below 6) and insoluble in neutral and basic aqueous solutions (pH being 6 or above).

To practice the method of this invention, an acidic solution containing a calcium-based mineral and a porous matrix are first obtained.

The acidic solution can be easily prepared by dissolving a calcium-based mineral in an aqueous solution containing either an organic acid (e.g., acetic acid or lactic acid) or a mineral acid (e.g., hydrochloric acid or sulfuric acid). It typically contains 1-20% by weight the calcium-based mineral, which can be obtained from a commercial supplier or prepared by a conventional method. Examples of the calcium-based mineral, either synthetic or naturally occurring, include apatite, calcium phosphate, calcium carbonate, anorganic bone, or a mixture thereof.

The porous matrix, of any desirable shape, can be metal-based or polymer-based. A metal-based matrix is made from a metal (e.g., titanium, copper, gold, silver, stainless steel, cobalt chromium alloy, gold alloy, or titanium alloy). A polymer-based matrix, on the other hand, is made from a biopolymer or a synthetic polymer. Examples of a biopolymer include proteins (e.g., collagen, elastin, or fibrin) and polysaccharides (e.g., cellulose, chitosan, alginic acid, and glycosaminoglycan). Examples of a synthetic polymer include polyglycolic acid or polylactic acid.

A skilled person in the art can prepare the above-described porous matrices by well-known methods. For examples, preparation of high-density collagen membranes is described in U.S. Pat. Nos. 6,599,524; 5,206,028; and 4,725,671 and preparation of low-density collagen sponges is described in U.S. Pat. Nos. 6,454,787; 5,116,552; and 3,157,524.

Once a porous matrix and an acidic solution containing a calcium-based mineral are obtained, one can immerse the matrix, partially if desirable, in the acidic solution for a predetermined length of time (e.g., 1-180 minutes) to hydrate the matrix. The matrix is then removed from the acidic solution. The thus-obtained matrix is subsequently exposed to an alkali. The alkali can be an organic or inorganic base in the form of a gas (e.g., gaseous ammonia or gaseous amine) or a liquid (e.g., triethylamine or a solution of ammonium hydroxide, sodium hydroxide, or potassium hydroxide). When a gaseous alkali is used, one can simply place the matrix in the vapor. When an alkali solution is used, one can spray it in mist particles onto the matrix. Upon contact with the matrix, the alkali neutralizes the acidic solution and raises its pH value to 6 or higher. As a result, the calcium-based mineral in the solution precipitates and deposits on the surfaces of the matrix (e.g., a metal-based or polymer-based matrix) or inside the matrix (e.g., a polymer-based matrix).

In the above-described method, if a porous polymer-based matrix is immersed in an acidic solution containing a calcium-based mineral, the acidic solution may penetrate into its body (i.e., the solid portion of the matrix) either through its exterior surfaces or through its interior surfaces that define pores. The amount of the solution absorbed into the body depends on the density of the body and the time length of immersion. The lower the density and the longer the immersion time, the greater amount of the acidic solution is absorbed. When the matrix is not fully soaked with the acidic solution or is fully soaked but, when later exposed to an alkali, is not fully neutralized, the bone implant thus obtained features a higher amount of the calcium-based mineral per unit volume on the surfaces and a lower amount of the calcium-based mineral per unit volume inside the body. The amount of the calcium-based mineral per unit volume on the surfaces can be determined by the ash test as follows: A surface layer is removed from the implant using a scalpel. The dimension of the sample is measured using a caliper and the volume of the surface layer is then calculated based on dimension measurements. The sample layer is then dried in vacuum for 24 hours and the dry weight determined. The dried implant is subsequently heated in a furnace at 500° C. for 4-6 hours to remove all the organic materials from the implant, and the residual weight of calcium-based mineral determined. The amount of mineral per unit volume in the surface can be calculated in unit of $g/cm^3$.

The amount of the calcium-based mineral per unit volume inside the body can also be determined by the ash method described above. Here, the volume of implant is sampled at a specific location within the implant.

The bone implant prepared by the method of this invention is useful for orthopedic tissue repair. It can also be used in dental surgery. For example, one can use a calcium phosphate-containing titanium implant to treat a bone defect. Other examples include using a calcium phosphate-containing collagen implant in dental or bone tissue regeneration.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein, including patents, are hereby incorporated by reference in their entirety.

Preparation of Purified Type I Collagen

Bovine deep flexor tendons were obtained from a USDA approved abattoir. After removal of fat and facia, tendons were rinsed with water, frozen, and sliced into slices (0.5 mm thick) with a meat slicer. Ten grams of the sliced tendons were extracted sequentially with 50 ml of water and 50 ml of 0.2 N HCl at room temperature for 24 hours. The tendons were rinsed with 50 ml of water and extracted with 50 ml of 0.75 M NaOH at room temperature for 24 hours. After removal of the basic solution, the tendons were treated with 0.1 N HCl until its pH value turned to 5 and then rinsed with water for several times. The thus-obtained tendons were extracted twice with 50 ml of isopropanol at room temperature for 16 hours and 24 hours, respectively, to remove fat. The tendons were then dried in a clean hood to provide purified Type I collagen.

Preparation of Solvent-Dispersed Collagen

Acid dispersion: 6.5 g of purified Type I collagen were dispersed in 1 L of 0.07 M lactic acid and homogenized with a Silverson homogenizer (East Longmeadow, Mass.). The dispersion was filtered through a 100 mesh stainless steel mesh filter. The filtrate was de-aired under vacuum and stored at 4° C. The collagen content in the dispersion was 0.62%

Alkaline dispersion: 10 g of purified Type I collagen were dispersed in 1 L of 0.005 M NaOH and homogenized with a Silverson homogenizer (East Longmeadow, Mass.). The dispersion was filtered through a 100 mesh stainless steel mesh filter. The filtrate was de-aired under vacuum and stored at 4° C. The collagen content in the dispersion was 0.95%

Collagen dispersions of various collagen contents were prepared in an analogous manner as described above.

Preparation of Porous Collagen Membrane Matrices

A collagen fiber was reconstituted by adjusting the pH of an acid dispersion having a 6.2% by weight collagen content in a 0.07 M lactic acid solution to the isoelectric point of collagen (pH 4.7-5.0). The reconstituted collagen fiber was partially dehydrated by mechanical compression, freeze-dried, and cross-linked with vapor formaldehyde (generated from a 2% formaldehyde solution at 22° C.) to obtain a porous membrane matrix. The matrices thus prepared had a density of 0.30-0.35 $g/m^3$.

Preparation of Porous Collagen Sponge Matrices

The pH of an alkaline dispersion having a 0.95% by weight collagen content in a 0.005 M NaOH solution was adjusted to 8.0 with 0.1 M HCl. The pH 8.0 dispersion was freeze-dried to provide a porous sponge matrix. The sponge matrix was then crosslinked with vapor formaldehyde (generated from a 2% formaldehyde solution at 22° C.) to obtain a porous collagen matrix. Matrices thus prepared had a density of 0.031-0.032 $g/m^3$.

A porous sponge matrix was also prepared as follows:

A collagen fiber was reconstituted by adjusting the pH of an acidic dispersion (0.07 M lactic acid) containing the collagen fiber (0.62%) to the isoelectric point of collagen (pH 4.7-5.0). The collagen fiber was coacervated, partially dehydrated, and freeze-dried to obtain a porous collagen sponge matrix. The freeze-dried porous collagen matrix was then cross-linked with vapor formaldehyde (generated from a 2% formaldehyde solution at 22° C.).

The matrices characterized were those fabricated from the alkaline dispersed collagen.

Incorporation of Calcium Phosphate into Porous Collagen Membrane Matrices

A porous collagen membrane matrix having a density of 0.30 $g/cm^3$ was immersed in an acidic solution of calcium phosphate (10% anorganic bone in 2N HCl) for a period of time sufficient to fully hydrate the matrix, i.e., about 60 minutes. The hydrated membrane matrix swelled as a result of the osmotic pressure developed inside. The matrix was then removed from the solution and exposed to an ammonia vapor (which became ammonium hydroxide in contact with water) to neutralize the acidic solution to a pH of 7 to 8. As the calcium phosphate precipitated out from the solution, a membrane matrix containing calcium phosphate was formed. The matrix was air dried. The neutralization of the membrane was further ensured by immersing the membrane in 0.05 M phosphate buffer for 60 minutes and the pH of the final solution was 7.0.

Four other calcium phosphate-containing membrane matrices were prepared in an analogous manner from matrices having densities of 0.33, 0.30, 0.33, and 0.35 $g/cm^3$, respectively.

Table 1 below shows the weight percent of calcium phosphate in each of the five thus-prepared calcium phosphate-containing membrane matrices, which ranges from 31.35% to 36.36%.

TABLE 1

Calcium phosphate-containing porous collagen membrane matrices

| Sample No. | density of dry pre-treated matrix (g/cm³) | weight of dry pretreated matrix (g) | weight of wet matrix (g) | weight of dry calcium-containing matrix (g) | % calcium phosphate |
|---|---|---|---|---|---|
| 1 | 0.30 | 0.0532 | 0.3407 | 0.0804 | 33.83 |
| 2 | 0.33 | 0.0657 | 0.3451 | 0.0957 | 31.35 |
| 3 | 0.30 | 0.0539 | 0.3228 | 0.0847 | 36.36 |
| 4 | 0.33 | 0.0646 | 0.3750 | 0.0963 | 32.92 |
| 5 | 0.35 | 0.0714 | 0.4034 | 0.1120 | 36.25 |
|  |  |  |  |  | 34.1 ± 2.2 (Avg ± SD) |

Incorporation of Calcium Phosphate into Porous Collagen Sponge Matrices

A porous collagen sponge matrix having a density of 0.032 $g/cm^3$ was immersed in an acidic solution of calcium phosphate (10% anorganic bone in 2 N HCl) for 60 minutes. The hydrated sponge matrix was removed from the solution and exposed to an ammonia vapor to neutralize the acidic solution to a pH of 7 to 8. As the calcium phosphate precipitated out from the solution, a sponge matrix containing calcium phosphate was formed. The matrix was then freeze-dried. The neutralization of the acid was further ensured by immersing the matrix in 0.05 M phosphate buffer for about 60 minutes and the pH of the final solution was 7.0. The calcium phosphate-containing matrix was then freeze-dried.

Three other calcium phosphate-containing collagen sponge matrices were in an analogous manner from matrices all having a density of 0.031 g/cm$^3$.

Table 2 below shows the weight percent of calcium phosphate in each of the four thus-prepared calcium phosphate-containing collagen sponge matrices, which ranges from 70.49% to 76.66%.

TABLE 2

Calcium phosphate-containing porous collagen sponge matrices

| Sample No. | density of dry pre-treated matrix (g/cm$^3$) | weight of dry pre-treated matrix (g) | weight of wet matrix (g) | weight of dry calcium-containing matrix (g) | % mineral |
|---|---|---|---|---|---|
| 1 | 0.032 | 0.0396 | 1.1492 | 0.1492 | 73.46 |
| 2 | 0.031 | 0.0366 | 1.0318 | 0.1257 | 70.88 |
| 3 | 0.031 | 0.0350 | 0.9492 | 0.1186 | 70.49 |
| 4 | 0.031 | 0.0361 | 1.3762 | 0.1547 | 76.66 |
| | | | | | 72.9 ± 2.8 (Avg ± SD) |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to usages and conditions. Thus, other embodiments are also within the claims.

What is claimed is:

1. A porous bone implant comprising a porous polymer-based matrix and a calcium-based mineral disposed on the surface of the matrix and inside the body of the matrix, wherein the amount of the calcium-based mineral per unit area on the surface of the matrix is greater than the amount of the calcium-based mineral per unit area inside the body of the matrix.

2. The bone implant of claim 1, wherein the matrix is a collagen-based matrix.

3. The bone implant of claim 1, wherein the matrix is a polysaccharide-based matrix.

4. The bone implant of claim 1, wherein the calcium-based mineral is apatite, calcium phosphate, calcium carbonate, or a mixture thereof.

5. The bone implant of claim 4, wherein the matrix is a collagen-based matrix.

6. The bone implant of claim 4, wherein the matrix is a polysaccharide-based matrix.

* * * * *